(12) United States Patent
Yamaguchi et al.

(10) Patent No.: US 9,700,260 B2
(45) Date of Patent: Jul. 11, 2017

(54) PORTABLE DEVICE AND HEARTBEAT REACHING TIME MEASUREMENT CONTROL METHOD

(71) Applicant: Seiko Epson Corporation, Shinjuku-ku (JP)

(72) Inventors: Eiichiro Yamaguchi, Matsumoto (JP); Reiko Sato, Azumino (JP)

(73) Assignee: Seiko Epson Corporation, Tokyo (JP)

( * ) Notice: Subject to any disclaimer, the term of this patent is extended or adjusted under 35 U.S.C. 154(b) by 57 days.

(21) Appl. No.: 14/506,464

(22) Filed: Oct. 3, 2014

(65) Prior Publication Data

US 2015/0099991 A1 Apr. 9, 2015

(30) Foreign Application Priority Data

Oct. 7, 2013 (JP) ................................. 2013-209932

(51) Int. Cl.
*A61B 5/024* (2006.01)
*A61B 5/00* (2006.01)

(52) U.S. Cl.
CPC .............. *A61B 5/486* (2013.01); *A61B 5/024* (2013.01); *A61B 5/02438* (2013.01);
(Continued)

(58) Field of Classification Search
CPC ..... A61B 5/024; A61B 5/02438; A61B 5/222; A61B 5/486; A61B 5/7282
See application file for complete search history.

(56) References Cited

U.S. PATENT DOCUMENTS 6,908,435 B1\* 6/2005 Mueller ................. A61B 5/681
600/500
7,314,450 B2\* 1/2008 Iwamiya ................ A61B 5/681
600/481

(Continued)

FOREIGN PATENT DOCUMENTS

| EP | 1 020 161 A1 | 7/2000 |
|----|--------------|--------|
| EP | 2 095 763 A1 | 9/2009 |
| JP | 2012-020134 A | 2/2012 |

OTHER PUBLICATIONS

Polar Coach Heart Rate Monitor—User's Manual, Dec. 31, 1999, http://www.polar.com/support_filed/en/C225742500419A8A422568A200438FD4/UserManualCoachUSA.pdf [retrieved on Feb. 12, 2015].

(Continued)

*Primary Examiner* — William Levicky
(74) *Attorney, Agent, or Firm* — Kilpatrick Townsend & Stockton LLP

(57) ABSTRACT

A heart rate of a user is monitored by a heart rate sensor set. On a touch panel, during execution of high-load exercise, time required from the start of the high-load exercise until the heart rate rises to reach a threshold of a lower limit of a target heartbeat zone of the high-load exercise is measured as a first threshold reaching time and displayed in a threshold-reaching-time display section. During execution of the following low-load exercise, time required from the start of the load exercise until the heart rate falls to reach a threshold of an upper limit of a target heartbeat zone of the low-load exercise is measured as a second threshold reaching time and displayed in the threshold-reaching-time display section.

15 Claims, 13 Drawing Sheets

(52) U.S. Cl.
CPC ............ *A61B 5/681* (2013.01); *A61B 5/7282* (2013.01); *A61B 5/742* (2013.01)

(56) References Cited

U.S. PATENT DOCUMENTS

| | | | |
|---|---|---|---|
| 8,900,099 B1* | 12/2014 | Boyette | A63B 24/0075 |
| | | | 482/1 |
| 2010/0268051 A1* | 10/2010 | Prasad | A61B 5/0002 |
| | | | 600/365 |
| 2012/0015778 A1 | 1/2012 | Lee et al. | |
| 2012/0173978 A1 | 7/2012 | Lee et al. | |
| 2014/0031703 A1* | 1/2014 | Rayner | A61B 5/02055 |
| | | | 600/484 |
| 2014/0141937 A1* | 5/2014 | Kim | A61B 5/222 |
| | | | 482/8 |

OTHER PUBLICATIONS

"Training Workout on the Garmin Forerunner 910XT", Apr. 24, 2012, XP054975740, https://www.youtube.com/watch?v=nbX2DV9zzDA [retrieved on Feb. 12, 2015].

"Garmin Forerunner 910XT owner's manual", Jan. 31, 2013, XP055169576, http:/www.manualagent.com/cdn/pdf/garmin/734-m-forerunner-910xt-manual-owner-s-manual.pdf [retrieved on Feb. 13, 2015].

Extended European search report, dated Mar. 2, 2015, of the corresponding European Application No. 14187454.5. (8 pages).

\* cited by examiner

PORTABLE DEVICE AND HEARTBEAT REACHING TIME MEASUREMENT CONTROL METHOD

BACKGROUND

1. Technical Field

The present invention relates to a portable device and the like.

2. Related Art

There is known a technique for causing a user, who trains for track and field, to carry an electronic device equipped with a receiver that receives a signal from a GPS (Global Positioning System) satellite and a sensor that measures a heartbeat (or an electronic device that communicates with the receiver and the sensor) and providing information beneficial for the training before the training, during the training, and after the training (see, for example, JP-A-2012-20134 (Patent Literature 1)).

With the technique, it is possible to provide moving speed and a highest heart rate during running on the basis of a monitoring result such as positioning information obtained from a signal of the GPS satellite and a measurement value of a heart rate. Providing various kinds of information using the monitoring result during the training is beneficial in improving a training effect.

Interval training is known as one kind of training for improving a cardiopulmonary function. As an evaluation index of the cardiopulmonary function by the interval training, time from the start of load exercise until a heart rate reaches a target heartbeat zone of the load exercise is conceivable.

More specifically, the time includes the following times.

1) time required from the start of high-load exercise until a heart rate rises to reach a first threshold set as a lower limit of a target heartbeat zone of the high-load exercise (hereinafter referred to as "first threshold reaching time")

2) time required from the start of a low-load exercise until a heart rate falls to reach a second threshold set as an upper limit of a target heartbeat zone of the low-load exercise (hereinafter referred to as "second threshold reaching time")

SUMMARY

An advantage of some aspects of the invention is to provide a technique for making it possible to provide a user with a significant index for determining improvement of the cardiopulmonary function.

A first aspect of the invention is directed to a portable device including: a heart-rate measuring unit configured to measure a heart rate; a threshold setting unit configured to set a threshold of the heart rate; a start detecting unit configured to detect the start of load exercise; a clocking unit configured to clock time from the detection of the start detecting unit until the heart rate reaches the threshold; and a display unit configured to display a result of the clocking.

According to the first aspect, it is possible to clock the time from the start of the load exercise until the heart rate reaches the threshold and provide a user with the time.

If a use in interval training is assumed, thresholds only have to be provided for respective kinds of the load exercise. That is, as a second aspect of the invention, the portable device according to the first aspect of the invention may be configured such that the load exercise includes high-load exercise and low-load exercise having different loads, the threshold setting unit sets a first threshold that the heart rate rises to reach according to the start of the high-load exercise, the start detecting unit detects the start of the high-load exercise, the clocking unit clocks a first time from the detection of the start of the high-load exercise until the heart rate reaches the first threshold (a first threshold reaching time), and the display unit displays the first time.

As a third aspect of the invention, the portable device according to the second aspect of the invention may be configured such that the threshold setting unit sets a second threshold that the heart rate falls to reach according to the start of the low-load exercise following the high-load exercise, the start detecting unit detects the start of the low-load exercise, the clocking unit clocks a second time from the detection of the start of the low-load exercise until the heart rate reaches the second threshold (a second threshold reaching time), and the display unit displays the second time.

As a fourth aspect of the invention, the portable device according to the third aspect of the invention may be configured such that the portable device further includes a start-condition setting unit configured to set a start condition for determining start timing of each of the high-load exercise and the low-load exercise, and the start detecting unit detects satisfaction of the start condition to detect the start of each of the high-load exercise and the low-load exercise.

The start condition can be set as appropriate. However, if a use in training based on running is assumed, as a fifth aspect of the invention, the portable device according to the fourth aspect of the invention may be configured such that the start-condition setting unit sets the start condition as time.

Alternatively, as a sixth aspect of the invention, the portable device according to the fourth aspect of the invention may be configured such that the portable device further includes a positioning unit, and the start-condition setting unit sets the start condition as a condition for a positioning position of the positioning unit.

A seventh aspect of the invention is directed to the portable device according to any of the first to sixth aspects of the invention, wherein the portable device further includes a storing unit configured to store detection order by the start detecting unit and a clocking result in the clocking unit in association with each other.

According to the seventh aspect, it is possible to refer to the clocking result by the clocking unit in time series after training.

An eighth aspect of the invention is directed to a heartbeat reaching time measurement control method including: measuring a heart rate; setting a threshold of the heart rate; detecting the start of a load exercise; clocking time until the heart rate reaches the threshold after the start of the load exercise is detected; and displaying a result of the clocking.

According to the eighth aspect, effects same as the effects of the first aspect are obtained.

BRIEF DESCRIPTION OF THE DRAWINGS

The invention will be described with reference to the accompanying drawings, wherein like numbers reference like elements.

DESCRIPTION OF EXEMPLARY EMBODIMENTS

Embodiment

Figure 1:
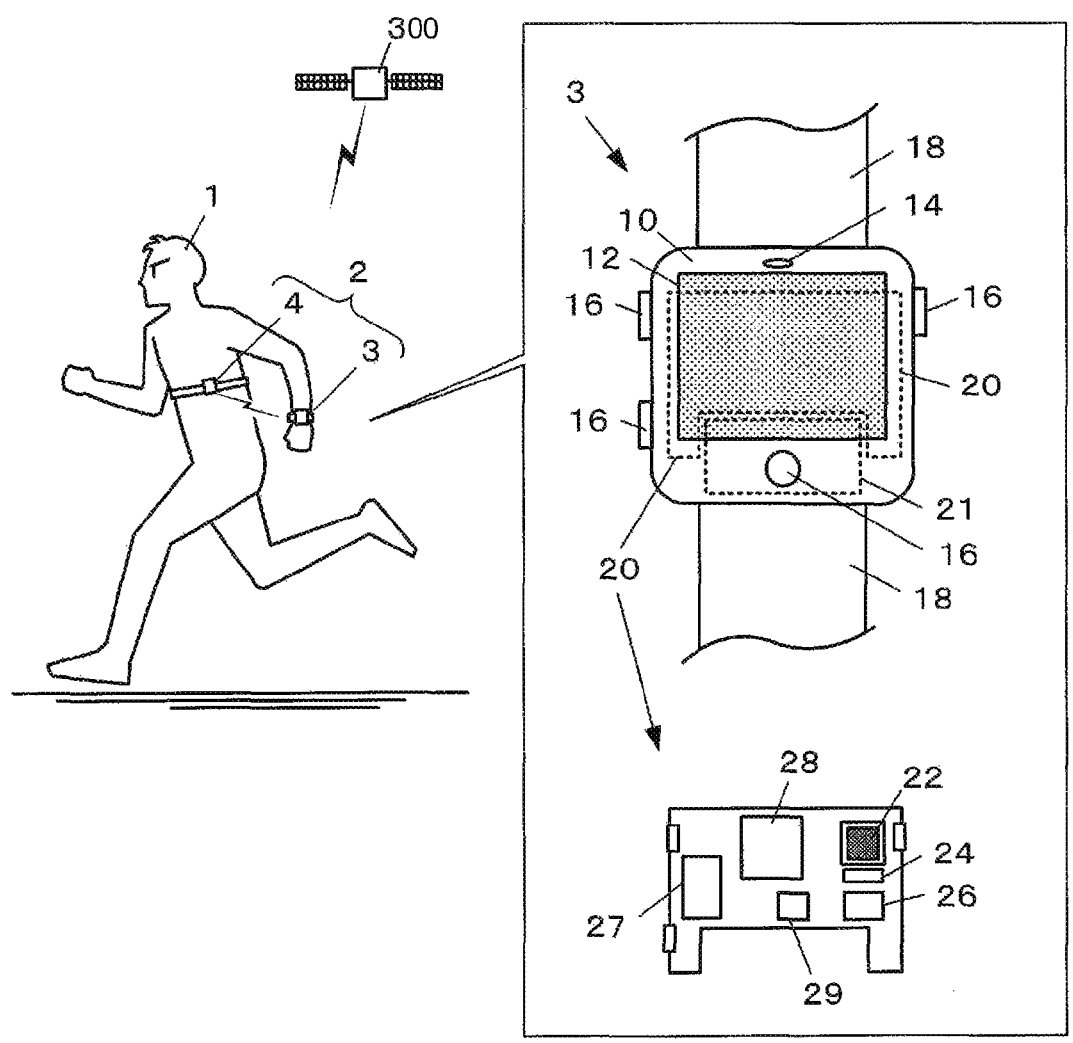
FIG. 1 is a diagram showing a configuration example of a portable device.

FIG. 1 is a diagram showing a configuration example of a portable device in an embodiment.

A portable device 2 in this embodiment is a portable electronic device wearable on the wrist or the arm of a user 1 like a wristwatch. The external appearance of the portable device 2 is a wearable computer classified into the wristwatch or a running watch.

The portable device 2 includes a main body unit 3 that performs main functions such as an arithmetic processing function and a display function and a heartbeat sensor set 4. The heartbeat sensor set 4 is a publicly-known body-wearable device that can cyclically measure a heartbeat of the user 1 and transmit heart rate data to the main body unit 3 by radio. In the example shown in FIG. 1, the heartbeat sensor set 4 is mounted on the chest of the user 1 by a band. However, the heartbeat sensor set 4 may be mounted on other body parts. The heartbeat sensor set can be integrated with the main body unit 3 as long as the heartbeat sensor set 4 can measure the heart rate.

The main body unit 3 includes a touch panel 12 and a speaker 14 on the upper surface of a main frame 10. The main body unit 3 includes one or a plurality of operation switches 16 for various operation inputs and a band 18 on side surfaces of the main frame 10. The band 18 is a mounting fixture. The main body unit 3 can be fixed to the wrist or the arm like the wristwatch or fixed to the ankle or the like by winding the band 18.

The main frame 10 forms an internal space excellent in airtightness and water proof properties. The main frame 10 incorporates a substrate 20 electrically connected to the touch panel 12, the speaker 14, the operation switches 16, and the like and a rechargeable battery 21 that supplies electric power to the substrate 20 and the like. A charging system for the rechargeable battery 21 can be set as appropriate.

For example, a configuration may be adopted in which the portable device 2 is set in a cradle connected to a home power supply and the rechargeable battery 21 is energized and charged through the cradle via an electric contact provided on the rear surface of the main frame 10.

The substrate 20 comprehensively controls the portable device 2. Specifically, the substrate 20 is mounted with a CPU (Central Processing Unit) 22, a main memory 24, a memory for measurement data 26, a vibrator 27, a positioning module 28, and a short range radio module 29. Beside, the substrate 20 can be mounted with ICs such as a power supply management IC and a driver IC for the touch panel 12 and electronic components as appropriate.

The main memory 24 is a storage medium that can store a computer program and initial setting data and store a calculated value of the CPU 22. The main memory 24 is realized using a RAM (Random Access Memory), a ROM (Read Only Memory), a flash memory, or the like as appropriate.

The memory for measurement data 26 is a data-rewritable nonvolatile memory and is a storage medium for storing data of a measurement result including position measurement information. In this embodiment, a flash memory is used as the memory for measurement data 26. However, other rewritable nonvolatile memories such as a ferroelectric memory and a magnetic resistance memory may be used.

The positioning module 28 is a positioning unit that can receive a signal provided from a position measuring system and output position measurement information to the CPU 22 at a predetermined cycle (e.g., every one second). In this embodiment, a GPS is used as the position measuring system. Therefore, the positioning module 28 can use a publicly-known "GPS module", "GPS receiver", or the like.

The position measurement information includes, for example, a positioning date and time (UTC: Coordinated Universal Time), a position coordinate (latitude and longitude), ground speed (a scalar amount), and a velocity azimuth (e.g., a traveling direction with the due north set to 0°). The ground speed and the velocity azimuth may be collectively calculated as velocity. The ground speed and the velocity azimuth are calculated on the basis of a Doppler shift (also called Doppler) that occurs in a signal transmitted from a GPS satellite 300. The position measurement information may include other information as appropriate.

Note that the system used for position measurement is not limited to the GPS. Other satellite navigation systems such as Galileo may be used. A radio wave from a base station, a ground position of which is known, may be additionally used. A position may be measured by inertial navigation using a speed sensor, an acceleration sensor, or the like.

Figure 2:
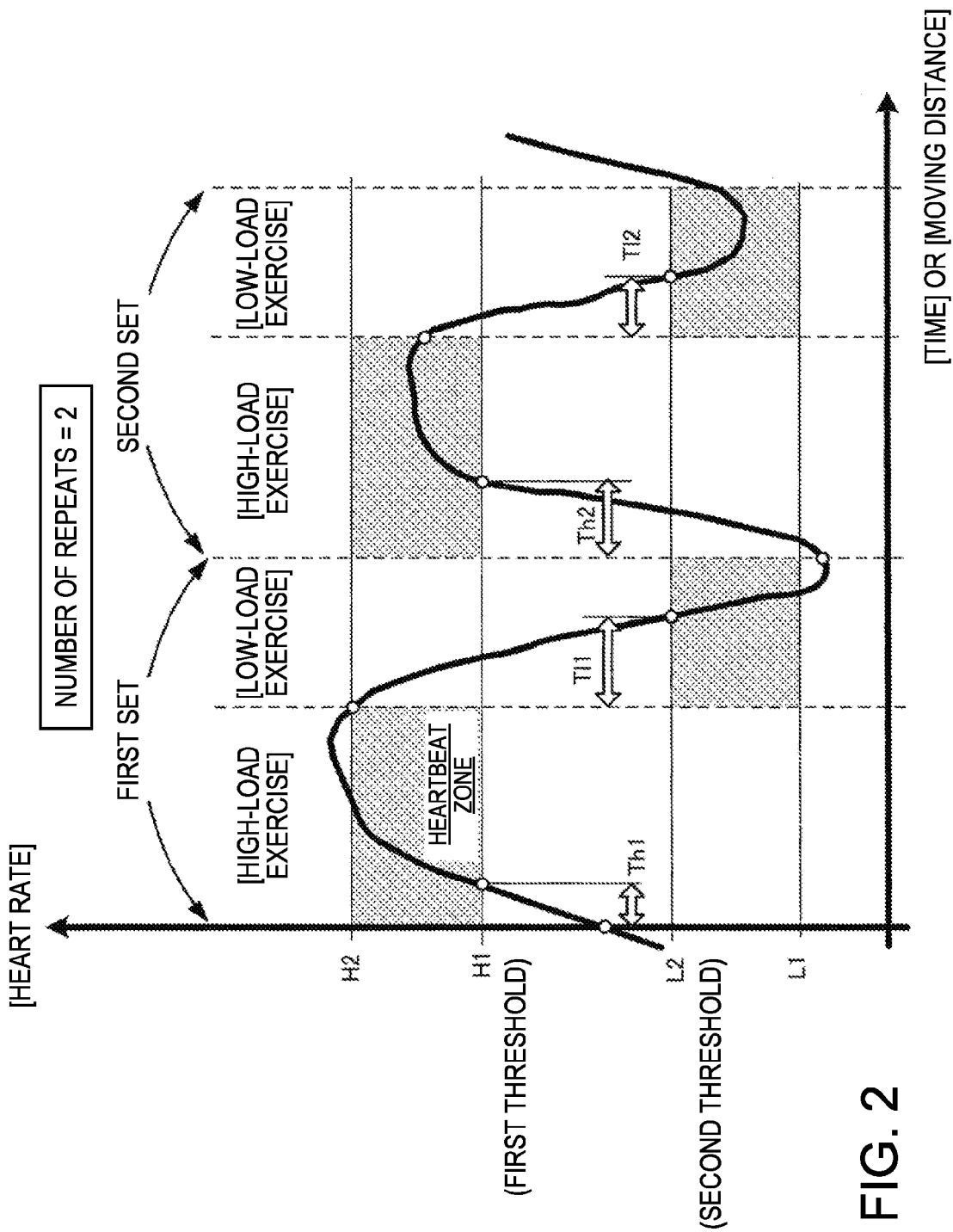
FIG. 2 is a diagram for explaining information concerning training provided to a user by the portable device.

FIG. 2 is a diagram for explaining information concerning training provided to the user 1 by the portable device 2 in this embodiment. FIG. 2 shows an example of a change in a heart rate in interval training.

The abscissa represents "time" or a "moving distance", which is a parameter for defining a break of the training. The ordinate represents a "heart rate", which is a parameter for defining a load of the training. A parameter value of the abscissa is obtained on the basis of the position measurement information obtained by the positioning module 28 of the main body unit 3 and local time. A parameter value of the ordinate is measured by the heartbeat sensor set 4.

As publicly known, the interval training is configured by repeating a plurality of sets, each including high-load exercise in which a relatively high heartbeat zone (H1 to H2) is set and low-load exercise in which a relatively low heartbeat zone (L1 to L2) is set. Start conditions and end conditions for the respective kinds of load exercise are defined by elapsed times or moving distances from the starts of the respective kinds of load exercise. Note that, in the example shown in the figure, the number of repeats is "2". However, actually, the user 1 can arbitrarily set the number of repeats.

In the interval training, a heart rate rises when the interval training is started from the high-load exercise. In the high-load exercise, a state in which the heart rate reaches the target heartbeat zone (H1 to H2) of the high-load exercise is maintained until the end condition for the high-load exercise is satisfied (that is, the start condition for the low-load exercise is satisfied). When the high-load exercise ends, the interval training immediately shifts to the low-load exercise. When the interval training shifts to the low-load exercise, the heart rate falls and soon reaches the target heartbeat zone (L1 to L2) in the low-load exercise. When the end condition for the low-load exercise is satisfied, one set ends. The satisfaction of the end condition for the low-load exercise means that the start condition for the high-load exercise is satisfied. The next set is started.

The portable device 2 in this embodiment can clock, as an elapsed time related to a change in the heart rate during the training, time until the heart rate reaches a threshold (an elapsed time from the start of the load exercise and is synonymous with time required until the heart rate reaches the threshold) and present the user 1 with the time.

Specifically, the portable device 2 can clock first threshold reaching times (Th1, Th2, . . . , and Thn [n is the number of sets]) until the heart rate rises according to the start of the high-load exercise and reaches a first threshold (H1) related to the target heartbeat zone (H1 to H2) of the high-load exercise and cause the touch panel 12 to display the first threshold reaching times. The portable device 2 can clock second threshold reaching times (Tl1, Tl2, . . . , and Tln [n is the number of sets]) until the heart rate falls according to the start of the low-load exercise and reaches a second threshold (L2) related to the target heartbeat zone (L1 to L2) of the low-load exercise and cause the touch panel 12 to display the second threshold reaching times.

In order to display the first threshold reaching time (Th) and the second threshold reaching time (Tl), it is necessary to set contents of the training in advance.

Figure 3:
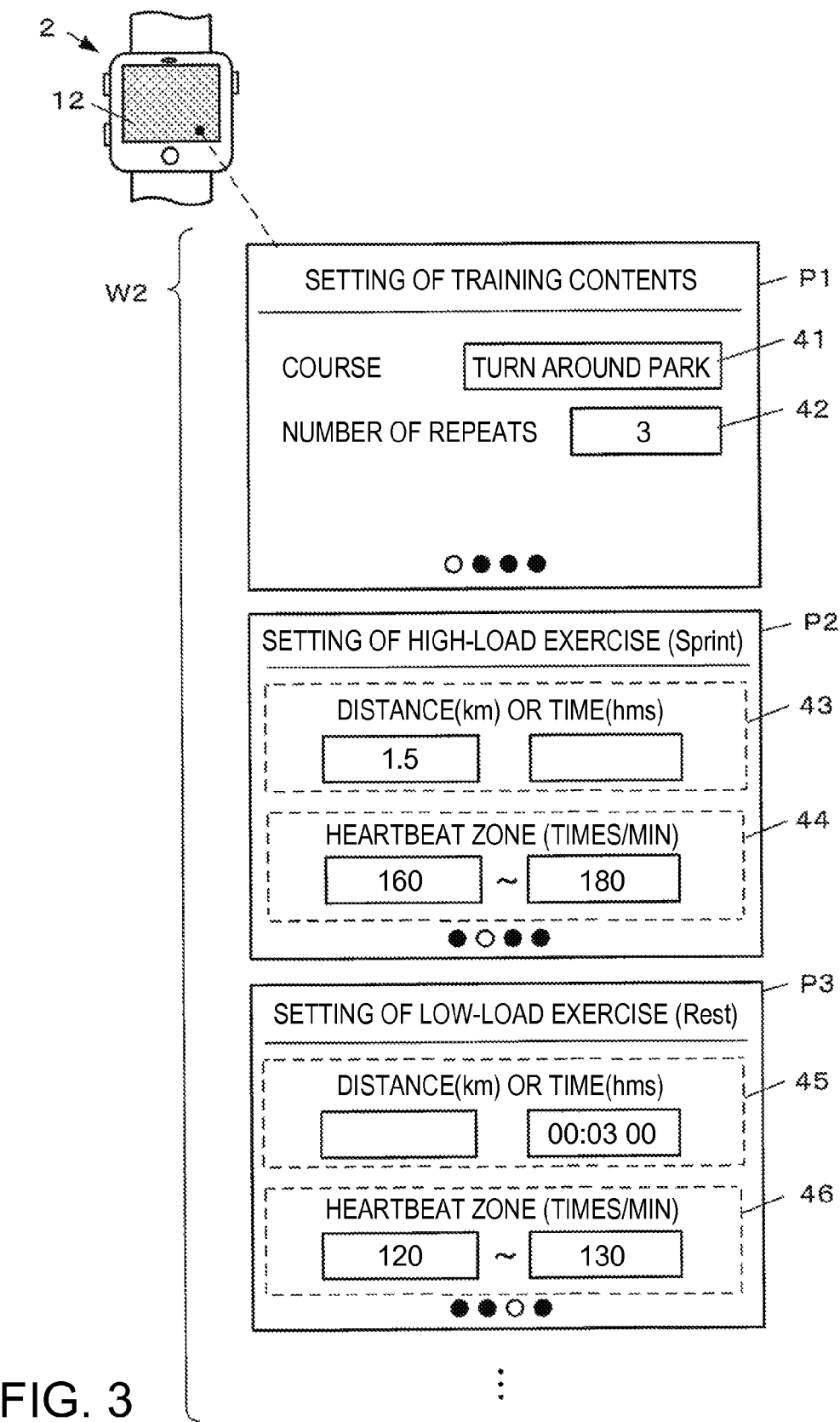
FIG. 3 is a diagram showing an example of a setting screen for setting contents of interval training.

FIG. 3 is a diagram showing an example of a setting screen W2 for setting contents of the interval training in this embodiment. The setting screen W2 in this embodiment is configured by a first page P1 to a third page P3.

The first page P1 is a page for defining basic parameter values concerning the entire interval training. In this embodiment, an input field 41 of training identification information for briefly identifying contents of the training and an input filed 42 of the number of repeats (the number of repeats of the set of the high-load exercise and the low-load exercise) are displayed. In the input field 41, for example, a course name arbitrarily determined by the user 1 and a name of the training can be input.

The second page P2 is a page for inputting parameter values for defining the high-load exercise. In this embodiment, an input field 43 of a moving distance or an elapsed time from the start of the high-load exercise, which is an end condition for the high-load exercise, and an input field 44 of an upper limit value and a lower limit value of a heart rate for defining the target heartbeat zone (H1 to H2) of the high-load exercise are displayed. In the following explanation in this embodiment, the end condition for the high-load exercise, that is, a start condition for the low-load exercise following the high-load exercise are set by a moving distance as a condition of a positioning position.

The third page P3 is a page for inputting parameter values for defining the low-load exercise. In this embodiment, an input field 45 of a moving distance or an elapsed time, which is an end condition for the low-load exercise, and an input field 46 of an upper limit value and a lower limit value of a heart rate for defining the target heartbeat zone (L1 to L2) of the low-load exercise are displayed. In the following explanation in this embodiment, the end condition for the low-load exercise, that is, a start condition for the high-load exercise of the next set following the low-load exercise is set as an elapsed time.

Note that the number of pages of the setting screen W2 and contents displayed on the pages can be changed as appropriate according to a display size of the touch panel 12 and an amount of contents of the training.

Concerning an input method to the input fields 41 to 46, a publicly-known technique can be applied as appropriate. For example, when the user 1 touches an input field to which the user 1 desires to input a parameter value, the input field is activated. It is also possible that a software ten key is screen-displayed and the user 1 inputs a parameter value by touching the ten key. Alternatively, the user 1 may input a parameter value by operating the operation switches 16. Note that, when any one of different kinds of parameter values is set as in the input field 43 and the input field 45, any one of the parameter values can be selectively set.

Figure 4A:
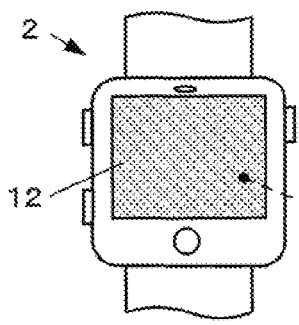
FIGS. 4A to 4C are diagrams showing display examples of elapsed times according to a change in a heart rate during training.
Figure 4B:
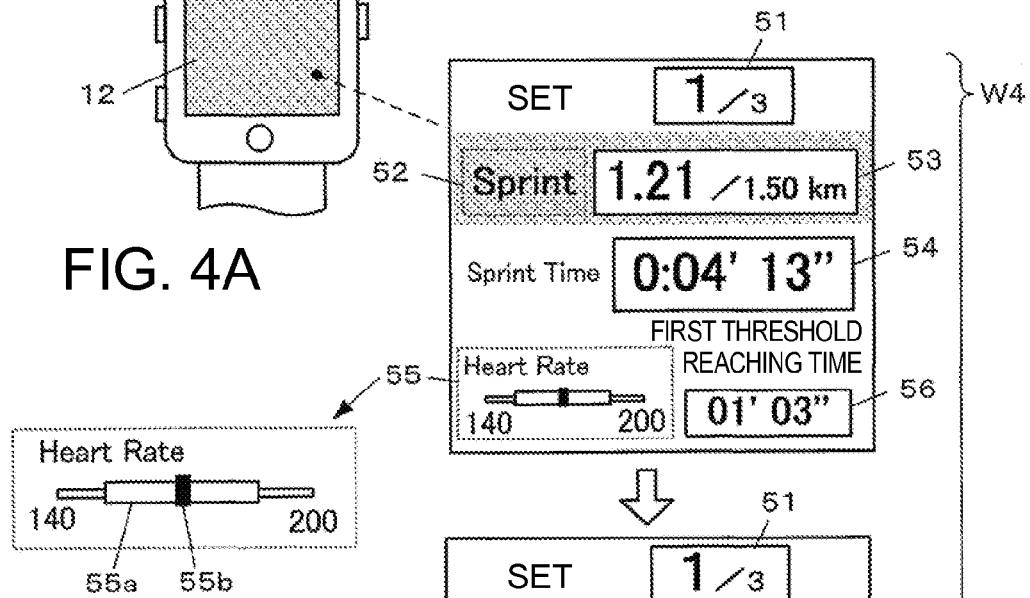
Figure 4B:
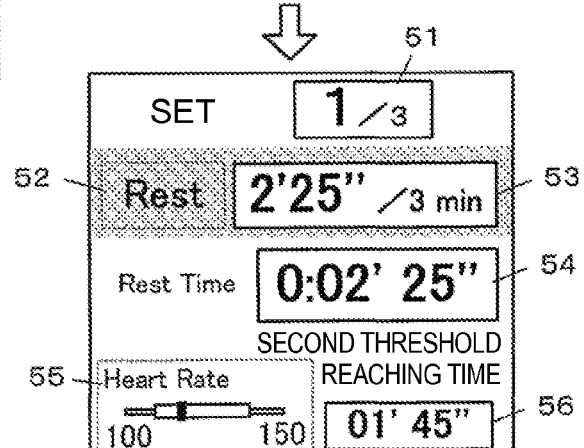
Figure 4C:
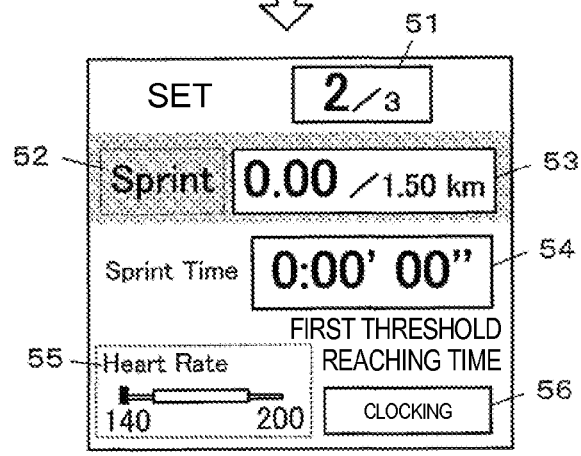

FIGS. 4A to 4C are diagrams showing display examples of elapsed times (the first threshold reaching time (Th) and the second threshold reaching time (Tl)) related to a change in a heart rate during the training. FIGS. 4A and 4B are screen display examples in a first set of the training. FIG. 4C is a display screen example in a second set following the first set.

A training support screen W4 displayed on the touch panel 12 during the training includes the following display sections.

1) a number-of-sets display section 51 showing the present number of sets 2) an exercise-type display section 52 showing a type of a load exercise 3) a comparative display section 53 for comparatively displaying an end condition for a load exercise currently being executed (i.e., a start condition for the next load exercise) and a present value of a parameter value for determining the condition Further, the training supporting screen W4 includes the following display sections 4) an elapsed-time display section 54 showing an elapsed time clocked from the start of the load exercise currently being executed 5) a heart-rate display section 55 for displaying a heart rate measured by the heartbeat sensor set 4

6) a threshold-reaching-time display section 56 for displaying time required from the start of the load exercise currently being executed until the heart rate reaches a heartbeat zone FIG. 4A shows display contents for the high-load exercise and is equivalent to a state during the high-load exercise of the first set. The number-of-sets display section 51 indicates that, in training, the number of repeats of which is "3", that is, training performed in three sets, the training is currently in a first set. One set of the training is the high-load exercise and the low-load exercise in this order. The exercise-type display section 52 displays "Sprint" that indicates the high-load exercise. The comparative display section 53 comparatively displays "1.5 km" equivalent to an end condition for the high-load exercise and a moving distance "1.21 km" to the present. The elapsed-time display section 54 displays an elapsed time from the start of the high-load exercise. The heart-rate display section 55 displays a heartbeat zone 55a of the load exercise currently being executed and the present (latest) heart rate 55b as a graph. Naturally, the elapsed-time display section 54 may display a heart rate as a text. The threshold-reaching-time display section 56 displays the first threshold reaching time (Th) until the heart rate rises according to the start of the high-load exercise and reaches the first threshold (H1) related to the target heartbeat zone (H1 to H2) of the high-load exercise.

FIG. 4B shows display contents for the low-load exercise and is equivalent to a state during the low-load exercise of the first set. The number-of-sets display section 51 indicates that, in the training performed in three sets in total, the training is currently in the first set. The exercise-type display section 52 displays "Reset" that indicates the low-load exercise. The comparative display section 53 indicates that the low-load exercise is set to be continued until an elapsed time from the start is 3 minutes and that 2 minutes 25 seconds elapses from the start of the low-load exercise. The elapsed-time display section 54 displays an elapsed time from the start of the low-load exercise. The heart-rate display section 55 displays the heartbeat zone 55a of the low-load exercise and the present heart rate 55b as a graph. The threshold-reaching-time display section 56 displays the second threshold reaching time (Tl) until the heart rate rises according to the start of the high-load exercise and reaches the second threshold (L2) related to the target heartbeat zone (L1 to L2) of the high-load exercise.

One set is configured by the high-load exercise and the low-load exercise. Therefore, when the end condition for the low-load exercise is satisfied, it is determined that the start condition for the high-load exercise of the next set is satisfied. Then, the next set is started.

FIG. 4C is equivalent to a state of the training support screen W4 immediately after the start of the high-load exercise of a second set. The number-of-sets display section 51 indicates that the training is currently in the second set. The exercise-type display section 52 displays "Sprint" that indicates the high-load exercise. Since the high-load exercise is just started, the comparative display section 53 indicates that the user 1 currently runs "0.00 km". The time display of the elapsed-time display section 54 is "0". Since the high-load exercise is just started, the clocking of the first threshold reaching time (Th) is not completed. Therefore, the threshold-reaching-time display section 56 displays a predetermined text that indicates that the clocking is being performed.

Figure 5:
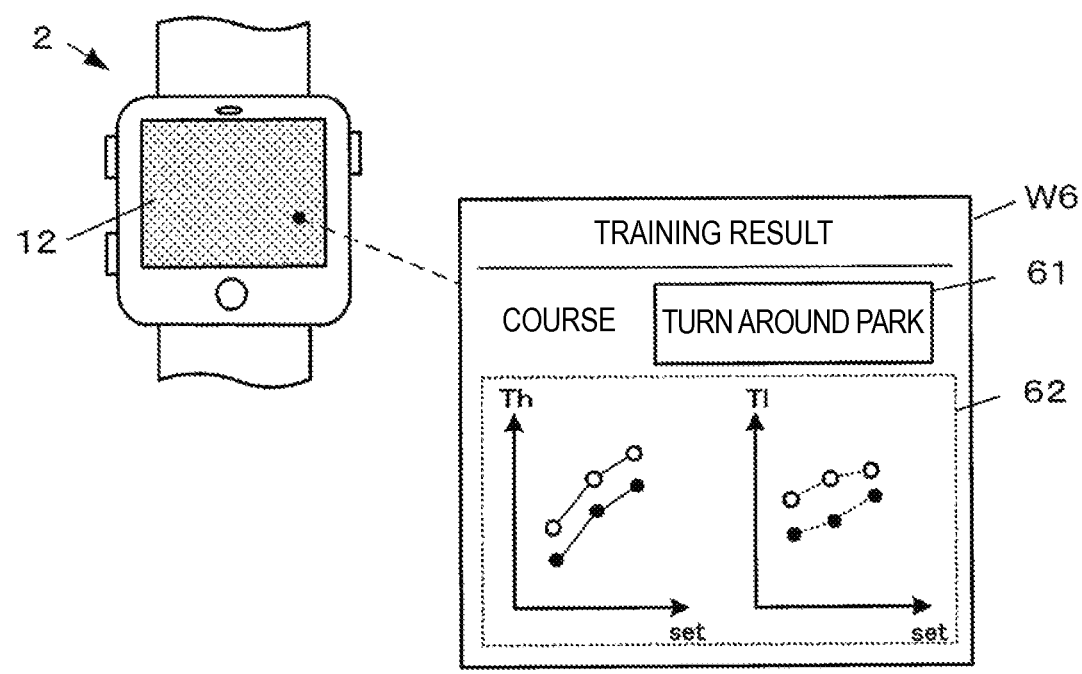
FIG. 5 is a diagram showing a display example of a training result display screen.

When the load exercise is carried out by the number of sets same as the number of repeats, it is regarded that the training ends. For example, as shown in FIG. 5, a training result display screen W6 is displayed. The display screen includes, for example, a training-identification display section 61 for displaying identification information of the training of this time and an elapsed time graph 62 for displaying the first threshold reaching time (Th) and the second threshold reaching time (Tl) for each of the sets. In the graph 62, the first threshold reaching time and the second threshold reaching time for each of the sets in a training result in the past are comparatively displayed. In an example shown in FIG. 5, a graph plotted by black circles indicates a training result of this type and a graph plotted by white circles indicate a training result of the last time (or an average of a predetermined number of times in the past). The training result of this time is displayed as a graph in comparison with the training result in the past of training of the same number of sets. Therefore, the user 1 can clearly and easily understand whether the cardiopulmonary function is improved.

Explanation of a Functional Configuration

A functional configuration in this embodiment is explained.

Figure 6:
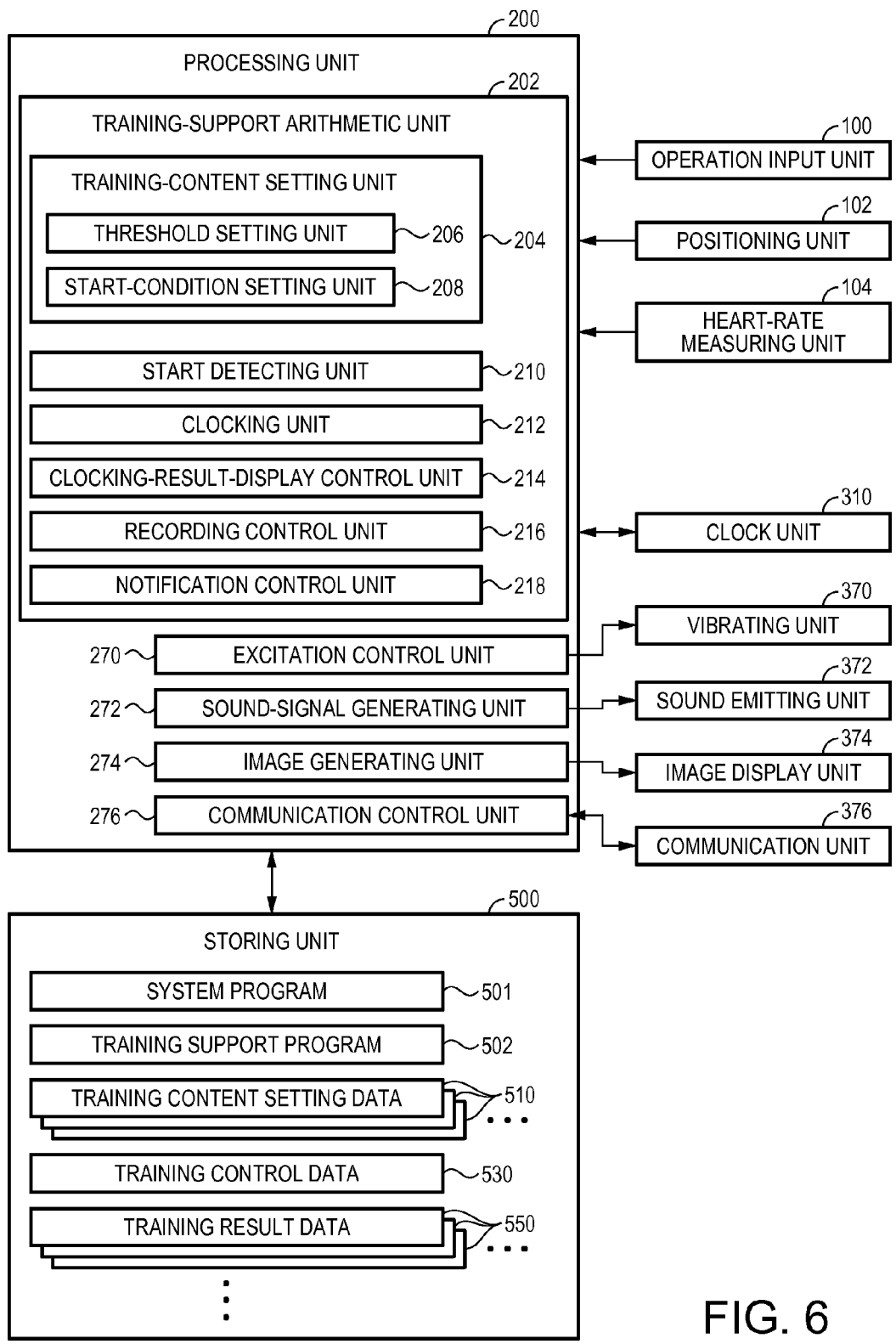
FIG. 6 is a functional block diagram showing a functional configuration example.

FIG. 6 is a functional block diagram showing a functional configuration example in this embodiment. The portable device 2 includes an operation input unit 100, a positioning unit 102, a heart-rate measuring unit 104, a processing unit 200, a clock unit 310, a vibrating unit 370, a sound emitting unit 372, an image display unit 374, a communication unit 376, and a storing unit 500.

The operation input unit 100 outputs an operation input signal to the processing unit 200 according to various operation inputs performed by the user 1. The operation input unit 100 can be realized by, for example, not only an element directly operated by a finger by the user 1 such as a button switch or a touch panel but also an element that detects exercise and posture such as an acceleration sensor, an angular velocity sensor, an inclination sensor, or a terrestrial magnetism sensor. The touch panel 12 and the operation switches 16 shown in FIG. 1 correspond to the operation input unit 100.

The positioning unit 102 receives a signal from the position measuring system, calculates position measurement information, and outputs the position measurement information to the processing unit 200. The positioning module 28 shown in FIG. 1 corresponds to the positioning unit 102.

The heart-rate measuring unit 104 measures a heart rate of the user 1 and outputs the heart rate to the processing unit 200. The heartbeat sensor set 4 shown in FIG. 1 corresponds to the heart-rate measuring unit 104.

The processing unit 200 is realized by a microprocessor such as a CPU or a GPU and an electronic component such as an IC memory. The processing unit 200 performs input and output control for data between the processing unit 200 and the operation input unit 100 and the functional units of the device including a storing unit 500. The processing unit 200 executes various kinds of arithmetic processing on the basis of a predetermined program, data, and the like and controls the operation of the portable device 2. In FIG. 1, the substrate 20 corresponds to the processing unit 200. The processing unit 200 corrects an hour (a clock hour) clocked by the clock unit 310 to a local standard hour using information concerning a position and a date and time included in the position measurement information calculated by the positioning unit 102.

The processing unit 200 in this embodiment includes a training-support arithmetic unit 202, an excitation control unit 270, a sound-signal generating unit 272, an image generating unit 274, and a communication control unit 276.

The training-support arithmetic unit 202 executes processing such as measurement, clocking, counting, and calculation of various parameter values such as a moving distance necessary for realizing training support.

The training-support arithmetic unit 202 in this embodiment includes a training-content setting unit 204 that performs control for setting contents of the interval training.

The training-content setting unit 204 performs control concerning display of the setting screen W2 explained in FIG. 3, inputs of texts and numerical values to the input fields 41 to 46, and recording of input various parameter values. The training-content setting unit 204 includes a threshold setting unit 206 that sets a threshold of a heart rate and a start-condition setting unit 208 that sets a start condition for determining start timing of each of the high-load exercise and the low-load exercise. Note that, in this embodiment, when one of the high-load exercise and the low-load exercise ends, the other is immediately started. Therefore, a start condition for determining start timing of one load exercise can be replaced with an end condition for determining end timing of the other load exercise.

The training-support arithmetic unit 202 includes a start detecting unit 210, a clocking unit 212, a clocking-result-display control unit 214, a recording control unit 216, and a notification control unit 218.

The start detecting unit 210 detects the start of the load exercise by sequentially determining, on the basis of position information, a heart rate, and a local standard hour (a clock hour) clocked by the clock unit 310, whether the end condition (i.e., the start condition) for the load conditions set by the start-condition setting unit 208 is satisfied.

The clocking unit 212 performs various kinds of clocking processing. For example, the clocking section 212 can clock elapsed times from the starts of the respective kinds of load exercise. In particular, the clocking unit 212 clocks times until a heart rate measured by the heart-rate measuring unit 104 with the detection by the start detecting unit 210 set as start timing reaches the thresholds (the first threshold (H1) and the second threshold (L2) in FIG. 2) set in the heartbeat zone of the respective kinds of load exercise, that is, the first threshold reaching time (Th) and the second threshold reaching time (Tl).

The clocking-result-display control unit 214 controls display of a result of the clocking by the clocking unit 212. The clocking-result-display control unit 214 performs display control related to the training support screen W4 shown in FIG. 4 and display control related to the training result display screen W6 shown in FIG. 5.

The recording control unit 216 performs time-series recording control of various measurement results and time-series recording control for various parameter values calculated during the training. Specifically, the recording control unit 216 performs control for associating, using time, the position measurement information (all or a part) obtained by the positioning unit 102 and the heart rate measured by the heart-rate measuring unit 104 and storing the position measurement information and the heart rate as so-called log data. The recording control unit 216 can perform control for storing a result clocked by the clocking unit 212 from the start to the end of the training in association with the start detection order by the start detecting unit 210.

The notification control unit 218 performs control for executing various kinds of notification related to the progress of the training. In this embodiment, the notification control unit 218 notifies the user 1 of breaks of the training using vibration and sound. Specifically, at given notification timings, the notification control unit 218 commands the excitation control unit 270 to generate and output a signal for generating vibration of a predetermined pattern to the vibrating unit 370. At the same notification timings, the notification control unit 218 commands the sound-signal generating unit 272 to generate and output a signal for emitting predetermined sound to the sound emitting unit 372. The notification timings are start timing of each of the high-load exercise and the low-load exercise and end timing of the training. The notification control unit 218 performs control such that vibrations of different patterns are generated and different sounds are emitted at the respective notification timings.

The excitation control unit 270 is equivalent to a driver circuit that generates and outputs a driving signal for the vibrating unit 370. The vibrating unit 370 is realized by a device that generates vibration like the vibrator 27 shown in FIG. 1.

The image generating unit 274 is realized by, for example, a CPU, a driver IC of a liquid crystal display, a GPU (Graphics Processing Unit), a program such as a video codec, and an IC memory for a rendering frame. The image generating unit 274 performs control for causing the image display unit 374 to display various images.

The image display unit 374 displays various images on the basis of a control signal inputted from the image generating unit 274. The image display unit 374 can be realized by an image display device such as a flat panel display. In this embodiment, the touch panel 12 shown in FIG. 1 corresponds to the image display unit 374. That is, the image display unit 374 functions as a display unit that displays the first threshold reaching time (Th) and the second threshold reaching time (Tl).

The communication control unit 276 executes data processing related to data communication and realizes exchange of data with an external device via the communication unit 376.

The communication unit 376 realizes data communication with the external device. The communication unit 376 is realized by, for example, a transceiver, a jack of a communication cable for wired communication, and a control circuit. The short range radio module 29 shown in FIG. 1 corresponds to the communication unit 376.

The clock unit 310 is configured by, for example, a clocking circuit including a crystal oscillator and clocks a local standard hour (a clock hour).

The storing unit 500 stores a computer program, various initial setting data, and the like for realizing functions for causing the processing unit 200 to comprehensively control the portable device 2. The storing unit 500 is used as a work area for arithmetic processing by the processing unit 200. The storing unit 500 can temporarily store, for example, a result of an arithmetic operation executed by the processing unit 200 according to various computer programs, data input from the operation input unit 100, and data of a measurement result measured by the positioning unit 102. Such a function is realized by, for example, a RAM or an IC memory such a flash memory. In FIG. 1, the main memory 24 and the memory for measurement data 26 mounted on the substrate 20 correspond to the storing unit 500.

The storing unit 500 in this embodiment stores a system program 501, a training support program 502, training content setting data 510, training control data 530, and training result data 550. Besides, the storing unit 500 can store a clocking timer, a flag, and the like as appropriate.

The system program 501 is a computer program for realizing a basic function of a computer in the portable device 2. The training support program 502 is application software read out and executed by the processing unit 200 to thereby realize a function of the training-support arithmetic unit 202. However, the training support program 502 may be incorporated as a part of the system program 501.

Figure 7:
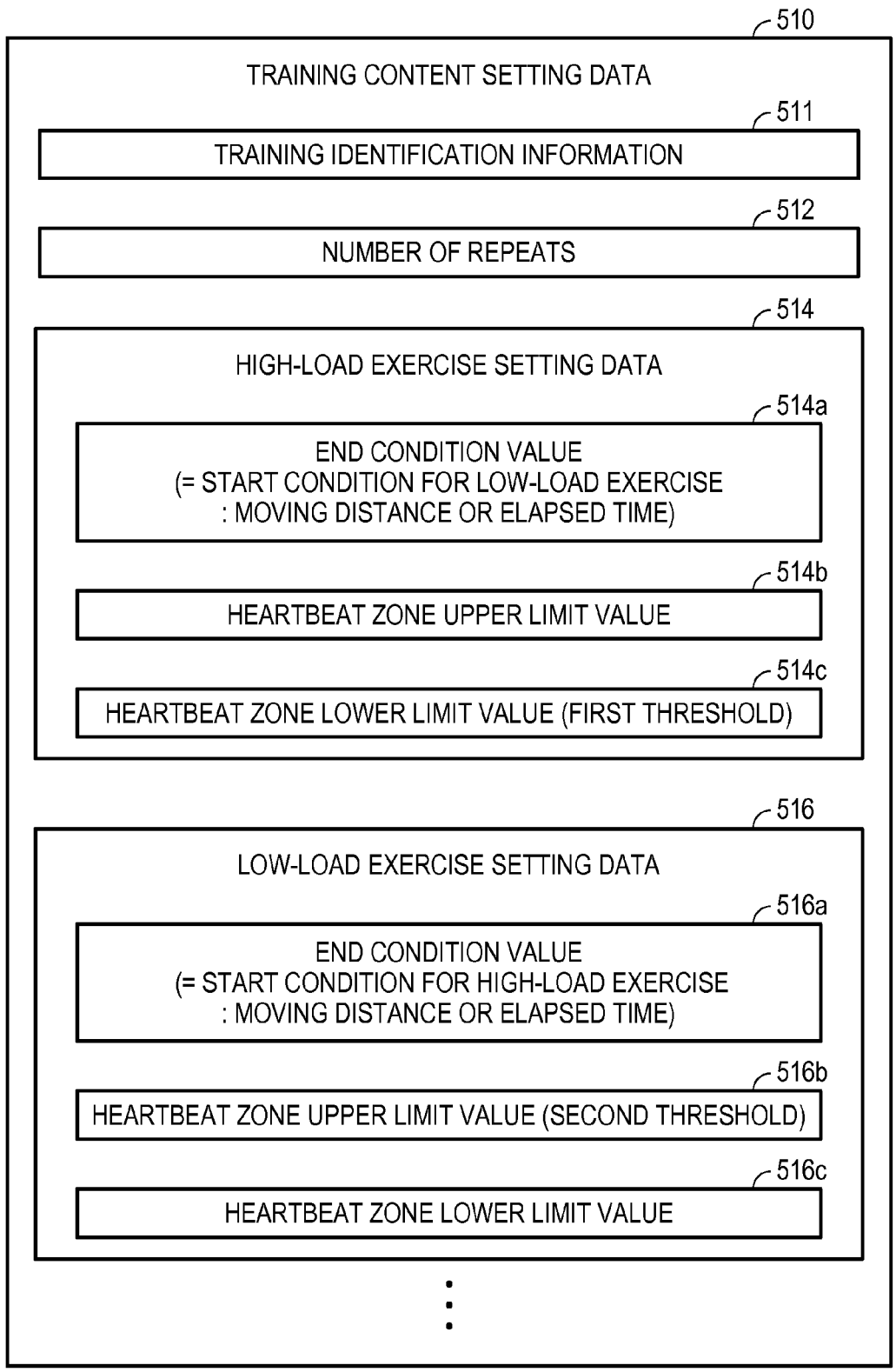
FIG. 7 is a diagram showing an example of a data configuration of training content setting data.

The training content setting data 510 is created for each of contents of the training by the training-content setting unit 204 and stores information for defining contents of the training input by the user 1. One training content setting data 510 includes, for example, as shown in FIG. 7, training identification information 511, the number of repeats 512, high-load exercise setting data 514, and low-load exercise setting data 516. Naturally, the training content setting data 510 may store data other than these data according to contents of training.

The high-load exercise setting data 514 includes an end condition value 514a for defining an end condition of the load exercise and a start condition of the low-load exercise and a heartbeat zone upper limit value 514b and a heartbeat zone lower limit value 514c set as targets in the load exercise. The heartbeat zone lower limit value 514c is the first threshold (H1) for clocking the first threshold reaching time (Th) in this embodiment.

The low-load exercise setting data 516 includes an end condition value 516a for defining an end condition of the load exercise and a start condition of the high-load exercise and a heartbeat zone upper limit value 516b and a heartbeat zone lower limit value 516c set as targets in the load exercise. The heartbeat zone upper limit value 516b is the second threshold (L2) for clocking the second threshold reaching time (Tl) in this embodiment.

Figure 8:
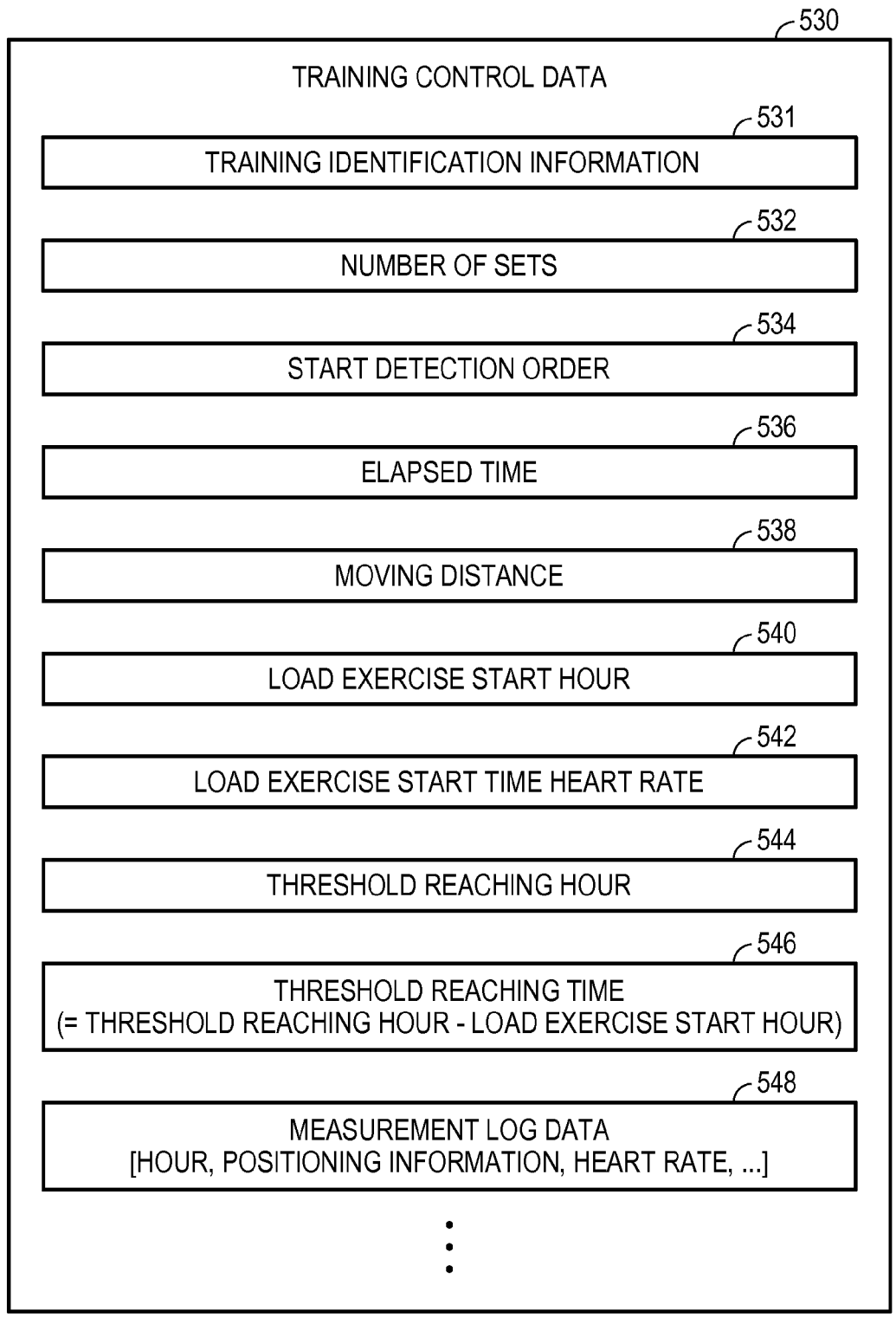
FIG. 8 is a diagram showing an example of a data configuration of training control data.

Referring back to FIG. 6, the training control data 530 stores various data that describes states of the interval training in this embodiment. For example, as shown in FIG. 8, the training control data 530 includes training identification information 531, the number of sets 532, start detection order 534, an elapsed time 536, a moving distance 538, a load exercise start hour 540, a load exercise start time heart rate 542, a threshold reaching hour 544, a threshold reaching time 546, and measurement log data 548. The training control data 530 is created and managed by the training-support arithmetic unit 202. Naturally, besides these parameter values, the training control data 530 can include values necessary for, for example, display control of various input screens.

In the training identification information 531, identification information of the training currently being executed is stored. An initial value of the number of sets 532 at the start of the training is "0". The number of sets 532 is counted up by "1" every time the high-load exercise and the low-load exercise are ended. An initial value of the start detection order 534 is "0". The start detection order 534 is counted up by "1" every time the high-load exercise or the low-load exercise starts.

The elapsed time 536 is reset at the start timings of the respective kinds of load exercise and stores a clocking value from the start of the load exercise.

The moving distance 538 is reset at the start timings of the respective kinds of load exercise and stores an integrated value of position displacement with respect to a positioning coordinate indicated by the position measurement information at the start timings.

The load exercise start hour 540 is data that describes timing when the load exercise is started. The load exercise start hour 540 is updated every time the load exercise is started. The load exercise start hour 540 stores, for example, time (clock time) at the timing and UTC included in the position measurement information.

The load exercise start time heart rate 542 is a heart rate at the timing when the load exercise is stared.

The threshold reaching hour 544 is data that describes timing when the heart rate reaches the threshold (the first threshold or the second threshold) related to the load exercise currently executed (it is seen that, if the start detection order 534 is an odd number, the high-load exercise is executed and, if the start detection order 534 is an even number, the low-load exercise is executed). The threshold reaching hour 544 stores, for example, time (clock time) at the timing or UTC included in the position measurement information.

The threshold reaching time 546 stores an elapsed time from the load exercise start timing, in other words, time required until the heart rate at the load exercise start timing reaches a threshold related to the load exercise. Specifically, the threshold reaching time 546 is time obtained by subtracting the load exercise start hour 540 from the threshold reaching hour 544.

The measurement log data 548 is array data in which a local standard hour (a clock hour), positioning information measured during the interval training, and a heart rate are associated and stored cyclically and in time series order.

Figure 9:
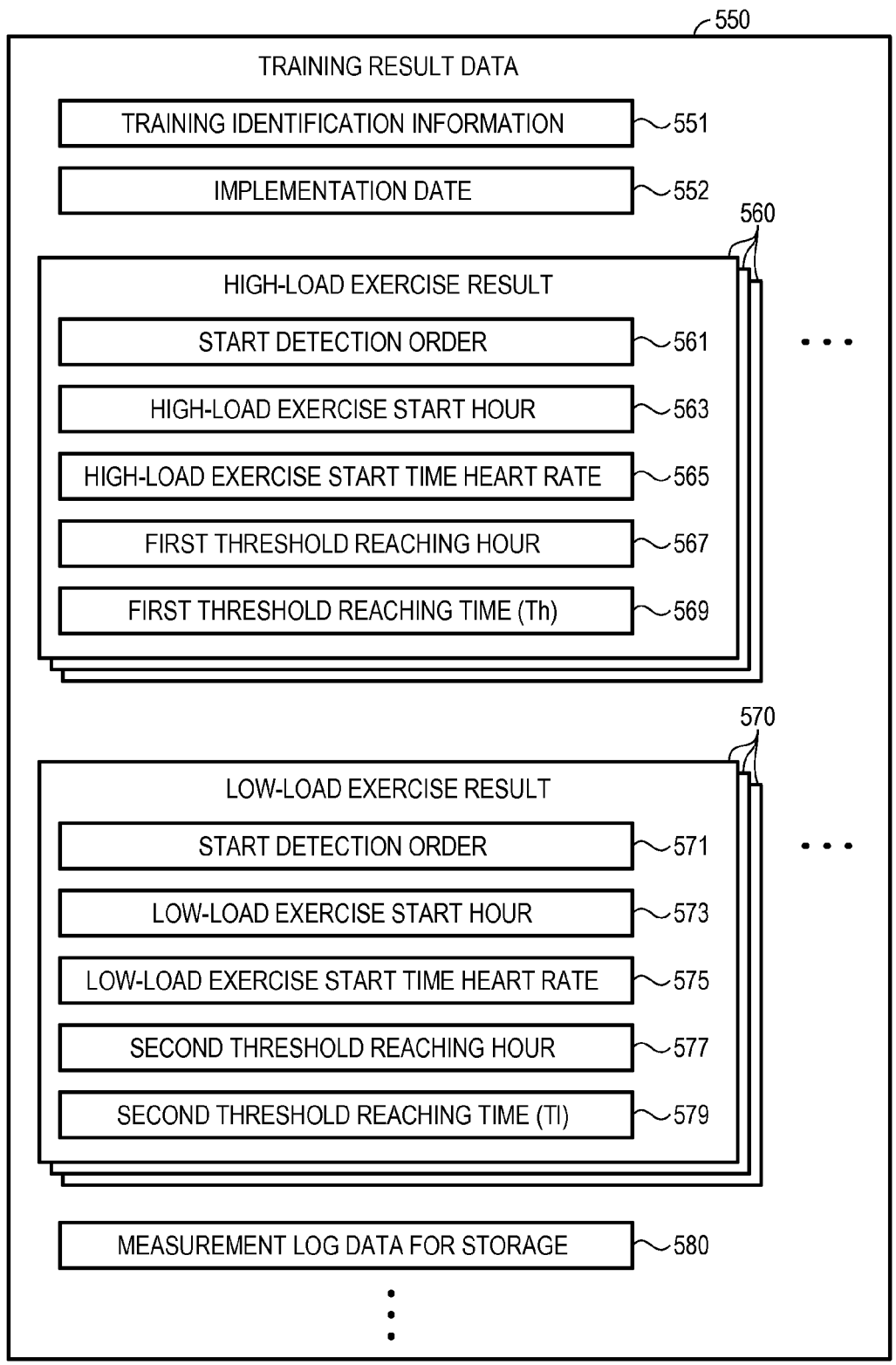
FIG. 9 is a diagram showing an example of a data configuration of training result data.

Referring back to FIG. 6, the training result data 550 is created and managed every time the interval training is carried out by the training-support arithmetic unit 202. One training result data 550 includes, for example, as shown in FIG. 9, training identification information 551, an implementation date 552, a high-load exercise result 560, a low-load exercise result 570, and measurement log data for storage 580.

The high-load exercise result 560 is created and stored for each high-load exercise.

One high-load exercise result 560 includes start detection order 561, a high-load exercise start hour 563, a high-load exercise start time heart rate 565, and a first threshold reaching hour 567. These are respectively copies of the start detection order 534, the load exercise start hour 540, the load exercise start heart rate 542, and the threshold reaching hour 544 stored in the training control data 530 (FIG. 8) at a point when the high-load exercise ends. The high-load exercise result 560 includes a first threshold reaching time (Th) 569. The first threshold reaching time (Th) 569 is calculated from a difference between the threshold reaching hour 544 and the load exercise start hour 540 at the point when the high-load exercise ends. An initial value of the first threshold reaching time (Th) 569 is set to a predetermined value that indicates that measurement is being performed.

The low-load exercise result 570 is created and stored for each low-load exercise.

One low-load exercise result 570 includes start detection order 571, a low-load exercise start hour 573, a low-load exercise start time heart rate 575, and a second threshold reaching hour 577. These are respectively copies of the start detection order 534, the load exercise start hour 540, the load exercise start time heart rate 542, and the threshold reaching hour 544 stored in the training control data 530 (FIG. 8) at a point when the low-load exercise ends. The low-load exercise result 570 includes a second threshold reaching time (Tl) 579. The second threshold reaching time (Tl) 579 is calculated from a difference between the threshold reaching hour 544 and the load exercise start hour 540 at the point when the low-load exercise ends. An initial value of the second threshold reaching time (Tl) 579 is set to a predetermined value that indicates that measurement is being performed.

The measurement log data for storage 580 is a copy of the measurement log data 548 stored in the training control data 530 (FIG. 8) at a point when the training ends.

Explanation of a Flow of Processing

The operation of the portable device 2 is explained.

Figure 10:
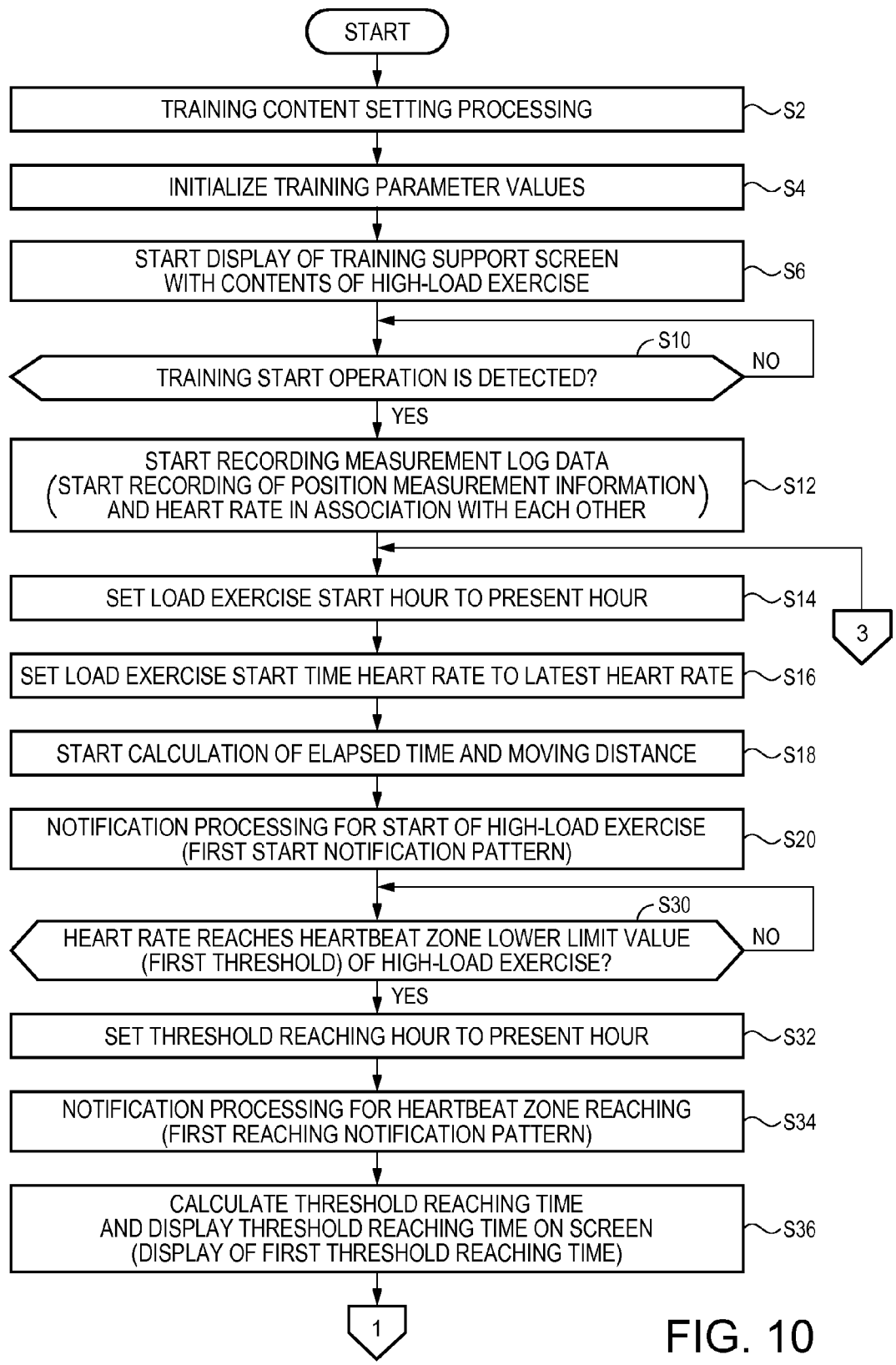
FIG. 10 is a flowchart for explaining a flow of processing concerning game support in the portable device.
Figure 11:
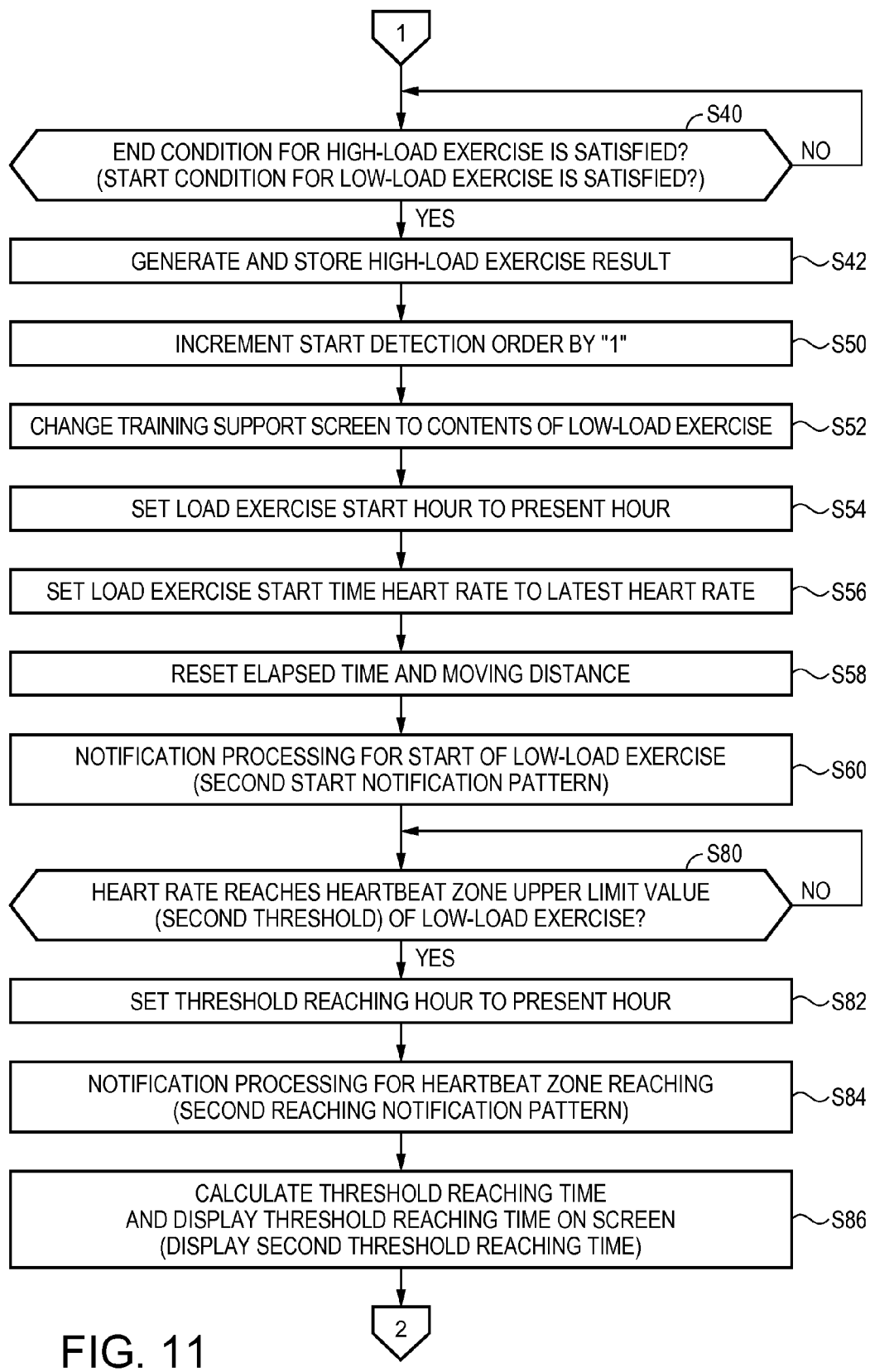
FIG. 11 is a flowchart following FIG. 10.
Figure 12:
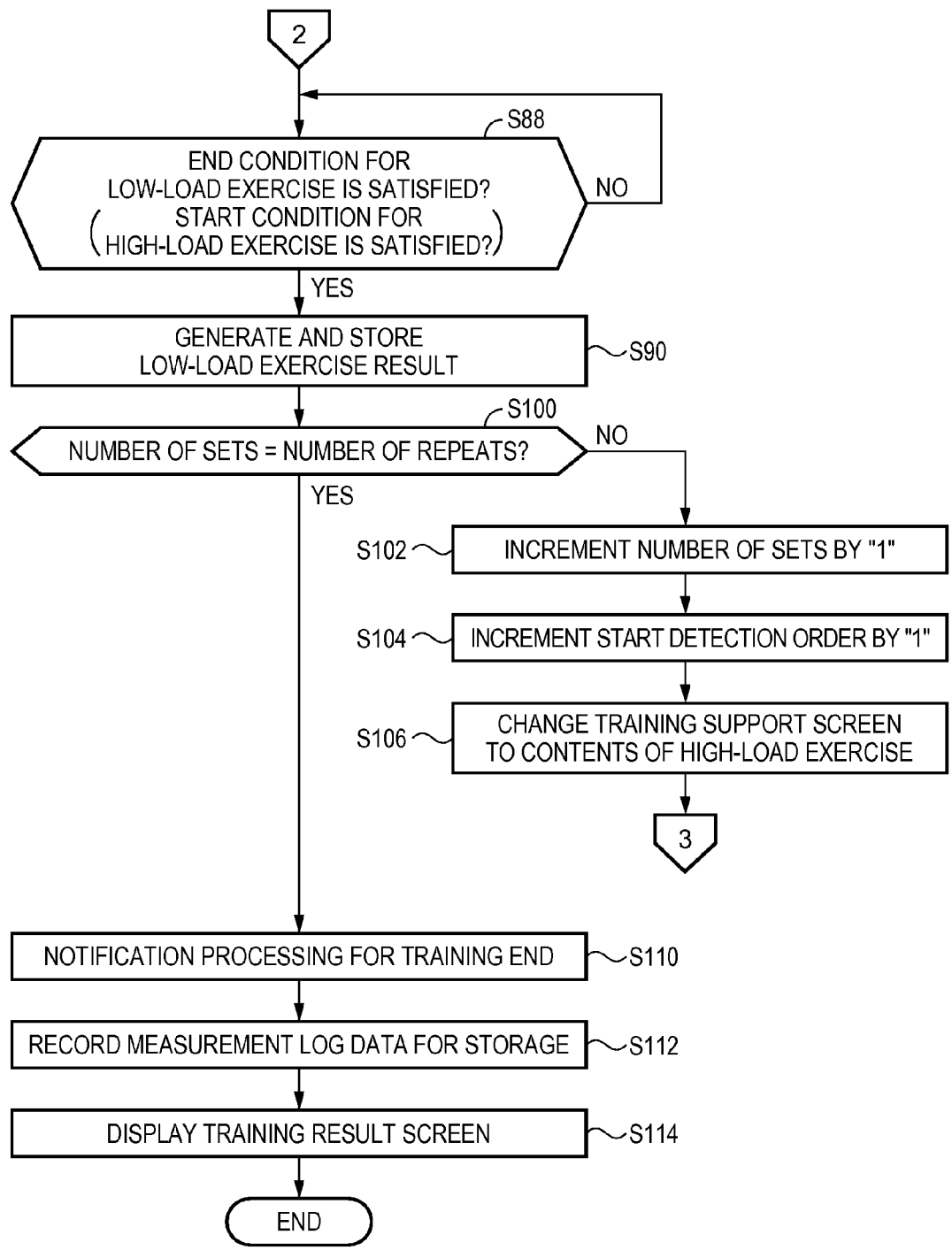
FIG. 12 is a flowchart following FIG. 11.

FIGS. 10 to 12 are flowcharts for explaining a flow of processing concerning game support in the portable device 2 in this embodiment. A flow of a series of processing explained below is realized by, for example, when actuation start operation for a predetermined training support function is detected, the processing unit 200 reading and executing the training support program 502. Alternatively, the program is already read and is being executed. The program is put in a standby state in which the program waits for the actuation start operation. Note that the position measurement by the positioning unit 102 and the measurement of a heart rate by the heart-rate measuring unit 104 are always performed if a power supply of the portable device 2 is on.

As shown in FIG. 10, first, the processing unit 200 executes training content setting processing (step S2). Specifically, the processing unit 200 causes the touch panel 12 to display the setting screen W2 (FIG. 3) for training contents and makes it possible to input various parameters for defining contents of training. An input result is stored in the storing unit 500 as the training content setting data 510. A storage area for the training control data 530 is secured. An input result to the input field 41 is stored in the training identification information 531. Note that, if an input result of identification information of the training is input to the input field 41, it is suitable to perform control for reading data of the same identification information from the existing training content setting data 510 and automatically displaying parameter values set in the other input fields.

Subsequently, the processing unit 200 initializes the training control data 530 (step S4).

Specifically, in the training identification information 531, the identification information of the training to be executed is already stored in step S2. Therefore, the identification information is kept stored. The number of sets 532 is set to "1". The start detection order 534 is set to "0". The elapsed time 536 and the moving distance 538 are set to "0". The load exercise start hour 540, the load exercise start time heart rate 542, and the threshold reaching hour 544 are set to predetermined values that mean undecided, standby, and unsettled.

Subsequently, the processing section 200 starts control for causing the touch panel 12 to display the training support screen W4 (FIG. 4) (step S6).

At this stage, contents of the training support screen W4 are the contents of the high-load exercise. That is, the present number of sets 532 is displayed in the number-of-sets display section 51. "Sprint" indicating the high-load exercise is displayed in the exercise-type display section 52. Since the calculation of the moving distance 538 is not started yet, a distance value for defining the end condition of the high-load exercise is displayed in the comparative display section 53. However, the display of the moving distance 538 is "0". Since the clocking of the elapsed time 536 is not started either, the elapsed-time display section 54 remains at "0". In the heart-rate display section 55, the latest heart rate is displayed. Since the threshold reaching hour 544 is still undecided, a predetermined text indicating that clocking is being performed is displayed in the threshold-reaching-time display section 56.

The user 1 performs a predetermined training start operation and starts the interval training. When detecting the operation (YES in step S10), the processing unit 200 regards that a start of first load exercise is detected and starts recording of the measurement log data 548 (step S12). The processing unit 200 sets the load exercise start hour 540 of the training control data 530 to the present hour (step S14) and sets the load exercise start time heart rate 542 to the latest heart rate (step S16).

Further, the processing unit 200 starts clocking of the elapsed time 536 and integration of the moving distance 538 (step S18).

At this stage, on the training support screen W4 of the touch panel 12, a value of the moving distance 538 is displayed in the comparative display section 53 and the elapsed time 536 is displayed in the elapsed-time display section 54. However, since the threshold reaching hour 544 is undecided, predetermined display indicating that clocking is being performed is kept performed in the threshold-reaching-time display section 56.

Subsequently, the processing unit 200 executes notification processing for notifying the user 1 of the start of the high-load exercise (step S20).

In the processing, the processing unit 200 performs control for causing the vibrator 27 to generate vibration of a predetermined first start notification pattern (e.g., three times of long vibration) and control for causing the speaker 14 to emit sound of the first start notification pattern (e.g., three times of long sound). According to the vibration and the sound emission, the interval training is started. It is possible to notify the user 1 that measurement of the high-load exercise is started.

After the measurement of the high-load exercise is started, when the heart rate reaches the heart rate zone lower limit value (the first threshold) 514c of the high-load exercise (YES in step S30), the processing unit 200 sets the threshold reaching hour 544 to the present hour (step S32). The processing unit 200 executes processing for notifying that the heart rate reaches the heartbeat zone of the high-load exercise (step S34). In the processing, the processing unit 200 performs control for causing the vibrator 27 to generate vibration of a predetermined first reaching notification pattern (e.g., one time of long vibration+one time of short vibration) and control for causing the speaker 14 to emit sound of the first reaching notification pattern (e.g., one time of long sound+one time of short sound).

Subsequently, the processing unit 200 subtracts the load exercise start hour 540 from the threshold reaching hour 544 to calculate and display the threshold reaching time 546 (step S36).

Then, the threshold reaching time 546 just calculated is displayed in the threshold-reaching-time display section 56 of the training support screen W4 of the touch panel 12.

Referring to the flowchart of FIG. 11, when the elapsed time 536 or the moving distance 538 reach the end condition value 514a of the high-load exercise setting data 514, the processing unit 200 determines that the end condition for the high-load exercise is satisfied, that is, the start condition for the next low-load exercise is satisfied (YES in step S40). The processing unit 200 generates a new high-load exercise result 560 (FIG. 9) on the basis of information concerning a training result obtained to that point and stores the high-load exercise result 560 (step S42).

Subsequently, the processing unit 200 increments the start detection order 534 by "1" (step S50) and changes the training support screen W4 to the contents of the low-load exercise (FIG. 4B) (step S52).

At this stage, the present number of sets 532 is displayed in the number-of-sets display section 51. "Rest" indicating the high-load exercise is displayed in the exercise-type display section 52. Since clocking of the elapsed time 536 is not started yet, a time value for defining the end condition for the low-load exercise is displayed in the comparative display section 53. However, a portion where the elapsed time 536 is displayed remains at "0". The elapsed-time display section 54 also remains at "0". However, the latest heart rate continues to be displayed in the heart-rate display section 55. Since the display contents of the training support screen W4 are switched, the second threshold reaching time is displayed in the threshold reaching hour 544. However, this is also undecided at this stage. Therefore, the predetermined display indicating that clocking is being performed is performed in the threshold-reaching-time display section 56.

Subsequently, the processing unit 200 stores the present hour in the load-exercise start hour 540 (step S54) and stores the latest heart rate in the load exercise start time heart rate 542 (step S56).

After resetting the elapsed time 536 and the moving distance 538, the processing unit 200 starts the clocking and the integration again (step S58) and executes notification processing for notifying the user 1 of the start of the low-load exercise (step S60). In the processing, the processing unit 200 performs control for causing the vibrator 27 to generate vibration of a predetermined second start notification pattern (e.g., three times of short vibration) and control for causing the speaker 14 to emit sound of the second start notification pattern (e.g., three times of short sound). According to vibration and the sound emission, it is possible to notify the user 1 that the measurement of the low-load exercise is started.

After the measurement of the low-load exercise is started, when the heart rate reaches the heartbeat zone upper limit value (the second threshold) 516b of the low-load exercise (YES in step S80), the processing unit 200 sets the threshold reaching hour 544 to the present hour (step S82) and executes processing for notifying that the heart rate reaches the heartbeat zone of the low-load exercise (step S84). In the processing, the processing unit 200 performs control for causing the vibrator 27 to generate vibration of a predetermined second reaching notification pattern (e.g., one time of long vibration+two times of short vibration) and control for causing the speaker 14 to emit sound of the second reaching notification pattern (e.g., one time of long sound+two times of short sound).

The processing unit 200 subtracts the load exercise start hour 540 from the threshold reaching hour 544 to calculate and display the threshold reaching time 546 (step S86). In the threshold-reaching-time display section 56 of the training support screen W4 of the touch panel 12, the threshold reaching time 546 just calculated is displayed. At this stage, the second threshold reaching time (Tl) is displayed (FIG. 4B).

Referring to the flowchart of FIG. 12, when the elapsed time 536 or the moving distance 538 reaches the end condition value 516a of the low-load exercise setting data 516, the processing unit 200 determines that the end condition for the low-load exercise is satisfied, that is, the start condition for the next high-load exercise is satisfied (YES in step S88). The processing unit 200 generates a new low-load exercise result 570 (FIG. 9) on the basis of information concerning a training result obtained to that point and stores the low-load exercise result 570 (step S90).

Subsequently, the processing unit 200 determines whether the present number of sets 532 (FIG. 8) reaches the number of repeats 512 (FIG. 7) (step S100).

If the present number of sets 532 does not reach the number of repeats 512 yet (NO in step S100), the processing unit 200 increments the number of sets 532 by "1" (step S102) and increments the start detection order 534 by "1" (step S104). The processing unit 200 returns the training support screen W4 to the contents of the high-load exercise (step S106). FIG. 4C is equivalent to a state in which the display contents are returned in the step. After switching the display contents of the training support screen W4, the processing unit 200 shifts to step S10 and starts measurement of the high-load exercise of the next set.

If the number of sets 532 reaches the number of repeats 512 (NO in step S100), the processing unit 200 executes notification processing for notifying the user 1 of the end of the training (step S110). In the processing, the processing unit 200 performs control for causing the vibrator 27 to generate vibration of a predetermined training end notification pattern (e.g., four sets of two times of short vibration) and control for causing the speaker 14 to emit sound of the training end notification pattern (e.g., four sets of two times of short sound).

The processing unit 200 copies the measurement log data 548 of the training control data 530 and stores the measurement log data 548 as the measurement log data for storage 580 of the training result data 550 (step S112), performs display control for the training result display screen W6 (FIG. 5) (step S114), and ends the series of processing related to the training support in this embodiment.

As explained above, according to this embodiment, it is possible to clock the first threshold reaching time (Th) required from the start timing of the high-load exercise until the heart rate rises and reaches the target heartbeat zone of the high-load exercise and the second threshold reaching time (Tl) required from the start timing of the low-load exercise until the heart rate falls to reach the target heartbeat zone of the low-load exercise and provides the user 1 with the first threshold reaching time (Th) and the second threshold reaching time (Tl).

Modifications

The embodiment to which the invention is applied is explained above. However, an application form of the invention is not limited to the embodiment. Addition, omission, and change of constituent elements can be applied as appropriate.

Figure 13:
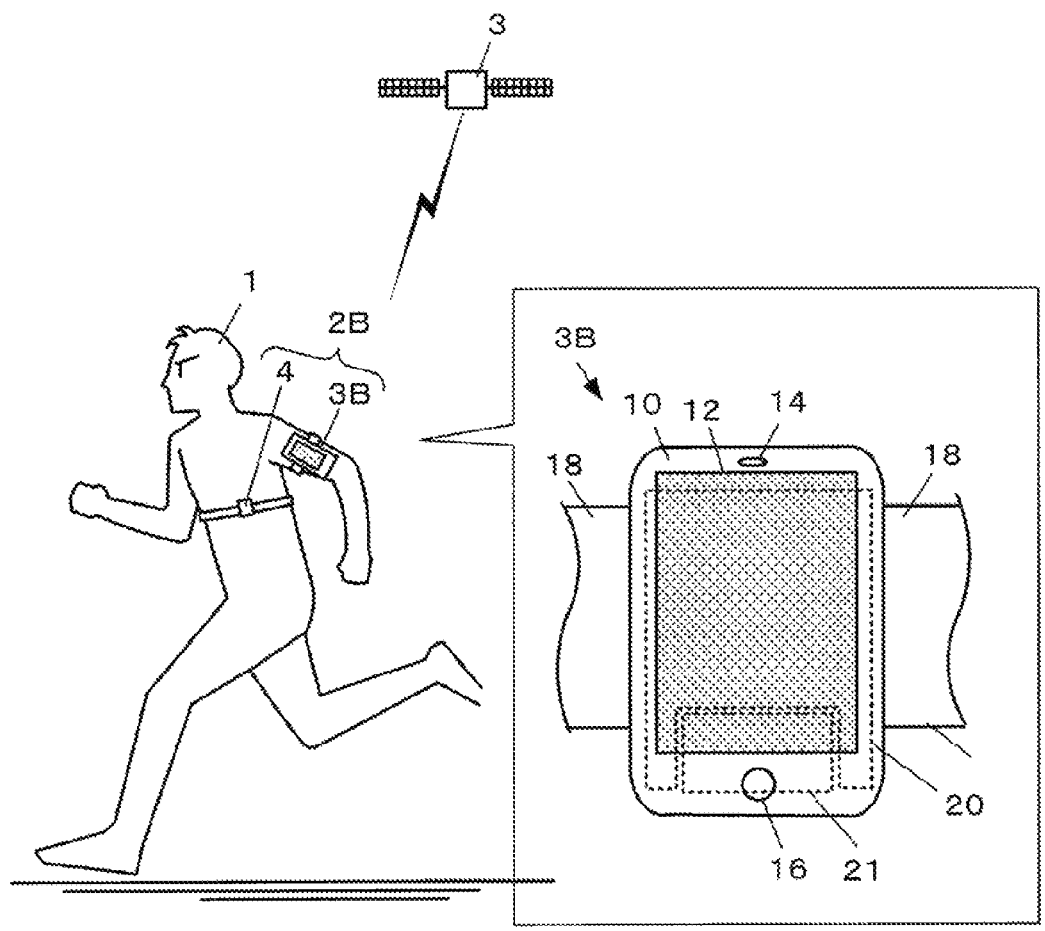
FIG. 13 is a diagram showing a modification of the portable device.

For example, in the embodiment, the portable device 2 is illustrated as the device mounted on the wrist of the user 1. However, a part of the body where the portable device 2 is mounted can be changed as appropriate. For example, like a portable device 2B shown in FIG. 13, a main body unit 3B may be a device assumed to be mounted on the upper arm by the band 18. Alternatively, the main body unit 3B may be designed to be mounted on the head like goggles by the band 18. Accordingly, the design of the portable device 2 is not limited to the wristwatch type and may be a tablet type, an action camera type, or a goggle type and can be set as appropriate. If the portable terminal 2 is sufficiently small, the portable device 2 may be provided in a structure like a temple of eyeglasses instead of the band 18 and designed in a glassware type.

In the example explained in the embodiment, the GPS is used as the position measuring system. However, the position measuring system may be other satellite positioning systems such as a WAAS (Wide Area Augmentation System), a QZSS (Quasi Zenith Satellite System), a GLONASS (GLObal NAvigation Satellite System), and GALILEO.

In the embodiment, the threshold reaching time 546 (FIG. 8) is calculated by subtracting the load exercise start hour 540 from the threshold reaching hour 544. However, the threshold reaching time 546 may be calculated by other methods. For example, the elapsed time 536 at timing when the heart rate reaches a target heartbeat zone of a load exercise executed at that point may be set as the threshold reaching time 546.

In the embodiment, the start conditions and the end conditions for the respective kinds of load exercise are the moving distances and elapsed times from the start of the load exercise. However, an exercise start location or an exercise end location may be defined. In that case, coordinate values only have to be stored in the end condition value 514a of the high-load exercise setting data 514 of the training content setting data 510 (FIG. 7) and the end condition value 516a of the low-load exercise setting data 516.

In the embodiment, the training result display screen W6 is displayed on the touch panel 12 of the portable device 2 of the wristwatch type. However, the clocking result may be transferred to the external device using the communication unit 376 to make it possible to check the training result display screen W6 from a display screen of the external device. With such a configuration, it is possible to easily check transition of a training result and transition of cumulative recording data using a large display unit. As the external device, a personal computer, a tablet, a smart phone, and the like can be used.

The entire disclosure of Japanese Patent Application No. 2013-209932, filed Oct. 7, 2013 is expressly incorporated by reference herein.

What is claimed is:

1. A portable device comprising:
a heart-rate measuring unit configured to measure a heart rate;
a positioning unit configured to:
receive a signal provided from a position measuring system and calculate position measurement information of the portable device at a predetermined cycle, and
determine a moving distance of the portable device;
a storing unit configured to store the position measurement information of the portable device calculated by the positioning unit;
a clock unit configured to clock an hour;
a clocking unit configured to determine an elapsed time;
a start detecting unit configured to:
detect a start of an interval exercise training based on a predetermined training start operation, and
detect, at a time later than detecting the start of the interval exercise training, a start of a load exercise based on a start condition previously set by a user of the portable device through a user interface, wherein the start condition for the start of the load exercise depends on the determined elapsed time if time was previously set by the user as the start condition or the determined moving distance if distance was previously set by the user as the start condition;
wherein the clocking unit is configured to clock time from the start of the load exercise until the heart rate reaches a threshold; and
a display unit configured to display a result of the clocking unit indicating the time elapsed until the heart rate reaches the threshold from the start of the load exercise, wherein the display unit is configured to display the user interface.

2. The portable device according to claim 1, further comprising a threshold setting unit configured to set the threshold.

3. The portable device according to claim 2, wherein
the load exercise includes high-load exercise and low-load exercise having different loads,
the threshold setting unit sets a first threshold that the heart rate rises to reach according to a start of the high-load exercise,
the start detecting unit detects the start of the high-load exercise,
the clocking unit clocks a first threshold reaching time from the detection of the start of the high-load exercise until the heart rate reaches the first threshold, and
the display unit displays the first threshold reaching time.

4. The portable device according to claim 3, wherein
the threshold setting unit sets a second threshold that the heart rate falls to reach according to the start of the low-load exercise following the high-load exercise,
the start detecting unit detects the start of the low-load exercise,
the clocking unit clocks a second threshold reaching time from the detection of the start of the low-load exercise until the heart rate reaches the second threshold, and
the display unit displays the second threshold reaching time.

5. The portable device according to claim 4, further comprising a start-condition setting unit configured to set a start condition for determining start timing of each of the high-load exercise and the low-load exercise, wherein
the start detecting unit detects satisfaction of the start condition to detect the start of each of the high-load exercise and the low-load exercise.

6. The portable device according to claim 5, wherein the start-condition setting unit sets the start condition as time.

7. The portable device according to claim 5, wherein
the start-condition setting unit sets the start condition as a condition for a positioning position of the positioning unit.

8. The portable device according to claim 1, wherein the storing unit is configured to store detection order by the start detecting unit and wherein the portable device further comprises a clocking result in the clocking unit in association with each other.

9. The portable device according to claim 1, further comprising a recording control unit configured to associate the position measurement information calculated by the positioning unit and the heart rate measured by the heart-rate measuring unit with time, and store the position measurement information and the heart rate.

10. The portable device according to claim 1, wherein an end condition for an end of the load exercise is set by the user of the portable device through the user interface prior to the start of the load exercise, and
wherein the heart-rate measuring unit is configured to measure the heart rate until the end of the load exercise even after the heart rate reaches the threshold from the start of the load exercise.

11. A heartbeat reaching time measurement control method comprising:
measuring a heart rate;
detecting a start of an interval exercise training based on a predetermined training start operation;
determining an elapsed amount of time or a moving distance since the start of the interval exercise training;
detecting, at a time later than detecting the start of the interval exercise training, a start of a load exercise based on a start condition previously set by a user, wherein the start condition for the start of the load exercise depends on the elapsed time if time was previously set by the user as the start condition or the moving distance if distance was previously set by the user as the start condition;
clocking time until the heart rate reaches a threshold after the start of the load exercise is detected; and
displaying a result of the clocking indicating the time elapsed until the heart rate reaches the threshold from the start of the load exercise.

12. The heartbeat reaching time measurement control method according to claim 11, further comprising setting the threshold of the heart rate before the load exercise is started.

13. A heart rate measuring system comprising:
a heart-rate measuring unit configured to measure a heart rate;
a positioning unit configured to:
receive a signal provided from a position measuring system and calculate position measurement information of the heart rate measuring system at a predetermined cycle,
determine a moving distance of the heart rate measuring system;

a storing unit configured to store the position measurement information of the heart rate measuring system calculated by the positioning unit;
a clock unit configured to clock an hour;
a clocking unit configured to determine an elapsed time;
a start detecting unit configured to:
  detect a start of an interval exercise training based on a predetermined training start operation, and
  detect, at a time later than detecting the start of the interval exercise training, a start of a load exercise based on a start condition previously set by a user of the heart rate measuring system through a user interface, wherein the start condition for the start of the load exercise depends on the determined elapsed time if time was previously set by the user as the start condition or the determined moving distance if distance was previously set by the user as the start condition;
wherein the clocking unit is configured to clock time from the start of the load exercise until the heart rate reaches a threshold; and
a display unit configured to display a result of the clocking unit indicating the time elapsed until the heart rate reaches the threshold from the start of the load exercise, wherein the display unit is configured to display the user interface,
wherein the heart-rate measuring unit and the clocking unit are configured by separate bodies, or the heart-rate measuring unit and the clocking unit are incorporated in a common case.

14. The heart rate measuring system according to claim 13, wherein
  the heart-rate measuring unit and the clocking unit are configured by separate bodies,
  the heart-rate measuring unit is arranged in a chest of a user, and
  the clocking unit is mounted on an arm of the user.

15. The heart rate measuring system according to claim 13, wherein
  the heart-rate measuring unit and the clocking unit are incorporated in a common case, and
  the case is mounted on an arm of a user.

* * * * *